United States Patent [19]

Stuckler

[11] Patent Number: 5,133,958
[45] Date of Patent: Jul. 28, 1992

[54] AGENT FOR NAIL, SKIN AND HAIR CARE

[76] Inventor: Erwin Stuckler, Haselbachstr. 18, D-7891 Weilheim/Ay, Fed. Rep. of Germany

[21] Appl. No.: 481,044

[22] Filed: Feb. 16, 1990

[30] Foreign Application Priority Data

Apr. 20, 1989 [CH] Switzerland ............ 01498890

[51] Int. Cl.$^5$ ............ A61K 7/48; A61K 7/06; A61K 7/075
[52] U.S. Cl. ............ 424/61; 424/70; 424/73
[58] Field of Search ............ 424/70, 73, 195.1, 61; 514/783; 252/DIG. 13

[56] References Cited

FOREIGN PATENT DOCUMENTS 289639 11/1988 European Pat. Off. .

OTHER PUBLICATIONS

Translation of E 289 639 (Nov. 9, 1988).

Primary Examiner—Thurman K. Page
Attorney, Agent, or Firm—Robert H. Montgomery

[57] ABSTRACT

Agents and processes for the care of nails, skin and hair, for combatting progressive hair loss and for stimulating fresh hair growth of human hair, containing in the form to be administered daily or as an amount of the agent to be taken daily;
a) from 80 to 500 mg of trigonelline and
b) from 1 to 5 mg of vitamin B6.

20 Claims, No Drawings

AGENT FOR NAIL, SKIN AND HAIR CARE

The invention relates to an agent for nail, skin and hair care and for combatting progressive hair loss and for stimulating fresh hair growth of human hair.

European patent application No 0 289 639 discloses an agent for reviving and for stimulating and strengthening hair growth. The agent includes the alkaloid trigonelline or trigonellinic acid. It also provides the teaching that vitamin B6 is to be added to the agent. However the European patent application does not disclose what amounts of the active substance or substances must be given in what sequence for example to the human body in order to arrive at the specified aim.

That is disadvantageous insofar as small doses of trigonelline do not exhibit the effect hoped for, while with excessively high levels of dosage, besides the cost implications, under some circumstances it is also necessary to reckon on side-effects which are undesirable in themselves.

It has now surprisingly been found that regular successes can be achieved with a novel trigonelline-bearing agent. It was also surprisingly found that the present agent is also valuable for the care of nails, skin and hair.

In accordance with the invention that is achieved by an agent containing in the form to be administered daily:
a) from 100 to 500 mg of trigonelline, and
b) from 1 to 5 mg of vitamin B6.

The term trigonelline is used to identify the compound 3-carboxy-1-methyl pyridinium hydroxide which is also known under the trivial or popular name of coffearine.

The amounts specified refer to the chemically pure form of the compounds.

Trigonelline can be used in synthesised form.

A particularly valuable and therefore also preferred form of trigonelline can be extracted from the seed of the goat's horn clover. Such extracts have already long been known per se and represent a mixture of various extractable components of the vegetable substance, in particular the seed of the plant of the genus Trigonella foenum graecum. Trigonelline can be obtained for example by one of the known extraction processes such as macerisation or percolation.

Vitamin B6 embraces the defined mixture of pyridoxine, pyridoxal and pyridoxamine. Vitamin B6 is sufficiently described in the literature and can be obtained in a synthetic fashion, a semi-synthetic fashion or from natural products.

A preferred agent, as described above, is one which contains:
a) from 100 to 400 mg of trigonelline, and
b) from 2 to 4 mg of vitamin B6.

The preferred agent also include those which contain from 10 to 50 mg of nicotinic acid and/or nicotinic acid amide.

A further preferred agent may contain from 1 to 4 mg of riboflavin.

Further preferred agents contain from 0.2 to 1 mg of folic acid.

The agents which are also preferred include those which contain from 5 to 25 mg of d-calcium pantothenate. Particularly preferred are agents which contain at least two of the substances nicotinic acid and/or nicotinic acid amide, riboflavin, folic acid and/or d-calcium pantothenate.

The specified substances are known per se and d-calcium pantothenate is also known from hair cosmetics.

It was found that the above-mentioned preferred substances which belong to the vitamin B group, in the specified amounts, together with the amounts according to the invention of trigonelline and vitamin B6, result in advantageously effective agents.

The agents according to the invention may also contain the amino acids cystine and/or lysine. Cystine and lysine are known compounds, lysine representing an essential amino acid and cystine representing a non-essential amino acid. Cystine per se has also been brought into use as a known substance for keratin formation in the hair cosmetic field.

Particularly preferred are agents which contain for example flower pollen, in turn containing riboflavin, zystin and rutin. The amount of pollen can be for example from 100 to 1,500 mg, desirably from 1,000 to 1,500 mg and preferably from 1,000 to 1,300 mg.

Also preferred is an agent which contains one or more substances from the series of calcium hydrogen phosphate, aqueous stinging nettle root extract and stinging nettle leaf extract, in particular from young leaves, thiamin nitrate (vitamin B1), vitamin B12, vitamin B8, methionine, a mixture of histidine, lysine and arginine, preferably in a ratio of 1:4:12, garlic oil and/or garlic extract or at least the compounds contained therein, aliin and/or aliicin, an extract from stinging nettle, coltsfoot, yarrow, rosemary, sage, horsetail, clover blossom and/or birch, a complex of vitamins A, E and/or F, vitamin H or sulphur-bearing amino acids.

Also preferred are agents, as described above, which contain one or more of the substances set out hereinafter, for example beer yeast, in which respect amounts of for example from 10 to 1,000 mg, desirably from 100 to 800 mg and preferably from 200 to 500 mg can be used, wheatgerm oil, for example in amounts of from 10 to 1,000 mg, advantageously from 100 to 800 mg and preferably from 200 to 500 mg, cod-liver oil, for example in amounts of from 10 to 1,000 mg, desirably from 100 to 800 mg and preferably from 200 to 500 mg.

The agent may possibly contain further auxiliary materials such as solvents, emulsifiers and/or stabilisers. Examples of solvents are ethyl alcohol, hydrated soya oil, soya oil, groundnut oil (Oleum arachidis) and water. Examples of emulsifiers are liquid soya lecithin and pure soya lecithin in powder form. Examples of stabilisers are nipastate and di-alpha-tocopherol. A particularly preferred composition, in its form for daily administration, contains from 80 to 500 mg of trigonelline or trigonellinic acid, preferably in the form of the extract from the plants of the sub-family Trigonella, from 1 to 5 mg of vitamin B6, from 10 to 50 mg of nicotinic acid or nicotinic acid amide, from 1 to 4 mg of riboflavin, from 0.2 to 1 mg of folic acid, from 5 to 25 mg of d-Ca-pantothenate and from 1,000 to 1,300 mg of flower pollen.

The agent can be administered in various ways. As the individual substances are soluble in water and/or ethyl alcohol, it is possible for example to make up a liquid preparation such as a syrup. Liquid forms of administration have the disadvantage that it is more difficult to provide the proper dose thereof. It is therefore advantageous for the agent according to the invention to be put into a solid form of administration thereof. Such forms are for example tablets, dragees (coated compressed pills or tablets), starch capsules or gelatine capsules. The active substances in the amounts provided in accordance with the present invention are subjected to processing in dependence on the respective form for administration thereof, for example with wheat starch, wheat flour or lactose, to form starch capsules. Another form is gelatine capsules, in which case the active substances must be received in a carrier such as a fat oil, a glycol, higher alcohol, or glycol ester, which obviously must be physiologically acceptable, and are processed with emulsifiers, for example from the series consisting of lecithins, gelatines or casein and possibly a permitted amount of at least one preserving agent such as PHB-ester, phenolic substances, sorbinic acid or aromatic or aliphatic alcohols, and if need be further auxiliary substances, to provide such capsules. The capsule material is preferably high-purity gelatine with and in particular without additives such as colouring agents.

The present invention also embraces a cosmetic process for the care of nails, skin and hair, for combatting progressive hair loss and for stimulating fresh hair growth of human hair, by means of trigonelline as an active substance, characterised in that an amount of from 80 to 500 mg of trigonelline together with from 1 to 5 mg of vitamin B6 is orally administered daily to the human body.

The embodiments of the agent, which are referred to hereinbefore as preferable, lead to preferred processes when such agents are used.

The use of the agent is intended in particular for human organisms and for combatting hair loss in that respect quite particularly in male human organisms, while a corresponding effect can also be envisaged in relation to other warm-blooded organisms with an at least partial covering of hair.

Besides combatting hair loss, the agent according to the invention also has an advantageous effect on the quality and appearance of the skin and nails.

So that the agent according to the invention can produce its effect, it is indicated that the amount according to the invention, which is to be taken daily, is to be taken for a period of at least 20 successive days. In accordance with natural hair growth, initial results can generally be detected after that period of time. There is no imperative upper limit in respect of time for administration of the agent, and the upper limit in respect of time depends primarily on the desired result.

Support for the effect by other forms of use of the agent according to the invention, for example by means of lotions, tonics, shampoos, creams or salves which are used externally at the appropriate points, according for example on the scalp, the skin generally and/or the finger and toe nails, are within the scope of the present invention.

Lotions, tonics, shampoos, creams and salves containing trigonelline and vitamin B6 in accordance with the present invention can also be used on their own.

A preferred form of application for external use, for nail, skin and hair care, for combatting progressive hair loss and for stimulating fresh hair growth of human hair, is for example a lotion or tonic with for example water, ethyl alcohol and/or propylene glycol as a carrier, containing from 300 to 600 mg, preferably 500 mg of trigonelline or trigonellinic acid from 5 to 15 mg, preferably 10 mg, of vitamin B6, from 30 to 50 mg, preferably 40 mg, of nicotinic acid and/or nicotinic acid amide and from 60 to 100 mg, preferably 80 mg, of d-Ca-pantothenate, in each case with respect to 100 ml of lotion. Further valuable substances of which one or more may be contained in the lotion are from the series of tree lichen extract, horse chestnut extract, vitamin complex of vitamins A, E, F and H, colloidal sulphur, garlic extract, phospholipids, polyoxyethylene sorbitan oleate, ethyl nicotinate, a mixture of histidine, lysine and arginine in a ratio of 1:4:12, an extract from stinging nettle, coltsfoot, yarrow, rosemary, sage, horsetail, clover blossom and birch, an aqueous extract from stinging nettle roots and young stinging nettle leaves, 2,4-pyrimidinediamine-6-(1-piperidinyl)-3-oxide, in particular in amounts of from 1,000 to 3,000 mg, preferably 2,000 mg, per 100 ml of lotion, and sulphur-bearing amino acids. The garlic extract contains for example the active substances aliin, aliicin and methyl allyl trisulphide either on their own or in a mixture with each other. The garlic extract is preferably used as an alcohol solution of 4 g per 100 ml of alcohol.

Other valuable substances which are of interest in one of the externally applicable forms of the agent according to the invention, for example in lotions, can be selected from the series of substances consisting of castor oil, Aloe vera or Jojoba oil.

The lotions may possibly contain tensides such as polyoxyethylene sorbitan oleate, lecithine and vegetable scents. A shampoo for hair care and for combatting progressive hair loss and for stimulating fresh hair growth of human hair contains from 300 to 700 mg, preferably 500 mg, of trigonelline or trigonellinic acid, from 5 to 15 mg, preferably 10 mg, of vitamin B6, from 30 to 50 mg, preferably 40 mg, of nicotinic acid and/or nicotinic acid amide, and from 60 to 100 mg, preferably 80 mg, of d-Ca-pantothenate, per 100 ml of shampoo.

Further valuable substances which can be contained in such shampoos are to be selected for example from the series consisting of tree lichen extract, horse chestnut extract, vitamin complex of the vitamins A, E, F and H, phospholipids, polyoxyethylene sorbitan oleate, ethyl nicotinate, a mixture of histidine, lysine, and arginine in a ratio of 1:4:12, an extract from stinging nettle, coltsfoot, yarrow, rosemary, sage, horsetail, clover blossom and birch, an aqueous extract from stinging nettle roots and young stinging nettle leaves and lecithin.

The above-mentioned components and active substances can be used in their form obtained by chemical or biochemical means or, if on a vegetable basis, in their naturally occurring form. Products obtained on a natural basis or from natural substances are preferred.

Finger and toe nails can also be treated with cosmetic formulations in the form of nail varnish which includes the agent.

I claim:

1. An agent for enhancing the cosmetic appearance of the human body, including in a form to be administered daily:
   a) from 80 to 500 mg of trigonelline, and
   b) from 1 to 5 mg of vitamin B6.

2. An agent according to claim 1 containing:
   a) from 100 to 400 mg of trigonelline and
   b) from 2 to 4 mg of vitamin B6.

3. An agent according to claim 1 further containing from 10 to 50 mg of a material selected from the group consisting of nicotinic acid and nicotinic acid amide and mixtures thereof.

4. An agent according to claim 1 further containing from 1 to 4 mg of riboflavin.

5. An agent according to claim 1 further containing from 0.2 to 1 mg of folic acid.

6. An agent according to claim 1 further containing from 5 to 25 mg of d-calcium pantothenate.

7. An agent according the claim 1 further containing the amino acids selected from the group consisting of cystine and lysine and mixtures thereof.

8. The agent according to claim 1 further including a carrier where the carrier is shampoo or hair lotion.

9. A cosmetic process for combatting progressive hair loss and for stimulating fresh hair growth of human hair characterized in that an amount of from 80 to 500 mg of trigonelline together with from 1 to 5 mg of vitamin B6 is orally administered daily to the human body.

10. A cosmetic process for the care of nails and skin characterized in that an amount of from 80 to 500 mg of trigonelline together with from 1 to 5 mg of vitamin B6 is orally administered daily to the human body.

11. An agent according to claim 1 including in the form to be administered daily from 80 to 500 mg of a material selected from the group consisting of trigonelline and trigonellinic acid and mixtures thereof, from 1 to 5 mg of vitamin B6, from 10 to 50 mg of a material selected from the group consisting of nicotinic acid and nicotinic acid amid and mixtures thereof, from 1 to 4 mg of riboflavin, from 0.2 to 1 mg of folic acid, from 5 to 25 mg of d-Ca-pantothenate and from 1,000 to 1,300 mg of flower pollen.

12. A lotion or tonic for enhancing the cosmetic appearance of the human body, containing water, a material selected from the group consisting of ethyl alcohol and propylene glycol and mixtures thereof as a carrier and from 300 to 700 mg, of a material selected from the group consisting of trigonelline and trigonellic acid and mixtures thereof, from 5 to 15 mg of vitamin B6, from 30 to 50 mg of a material selected from the group consisting of nicotonic acid and nicotonic acid amide and mixtures thereof and from 60 to 100 mg of a d-Ca-pantothenate, in each case with respect to 100 ml of lotion.

13. A shampoo for hair care, containing from 300 to 700 mg, preferably 500 mg, of trigonelline or trigonellic acid, from 5 to 15 mg, preferably 10 mg. of vitamin B6, from 30 to 50 mg, preferably 40 mg, of nicotinic acid and/or nicotinic acid amide, and from 60 to 100 mg, preferably 80 mg, or d-Ca-pantothenate, per 100 ml of shampoo.

14. An agent according to claim 11 wherein said trigonelline and trigonellic acid is in the form of the extract from the plants of the subfamily trigonella.

15. An agent for enhancing the cosmetic appearance of the human body, including in a form to be administered daily:
 a. from 80 to 500 mg of trigonelline, and
 b. from 1 to 5 mg of vitamin B6,
 said trigonelline and vitamin B6 being mixed in a carrier in a form to be ingested.

16. An agent according to claim 15 containing the amino acids selected from the group consisting of cystine and lysine and mixtures thereof.

17. An agent according to claim 15 containing:
 a) from 100 to 400 mg of trigonelline and
 b) from 2 to 4 mg of vitamin B6.

18. An agent according to claim 15 further containing from 10 to 50 mg of a material selected from the group consisting of nicotinic acid and nicotinic acid amide and mixtures thereof.

19. An agent according to claim 15 further containing from 1 to 4 mg of riboflavin.

20. An agent according to claim 15 further containing from 0.2 to 1 mg of folic acid.

* * * * *